United States Patent [19]
Takahashi et al.

[11] Patent Number: 6,151,956
[45] Date of Patent: *Nov. 28, 2000

[54] OIL DETERIORATION SENSOR

[75] Inventors: Toshimitsu Takahashi; Takuya Kondo, both of Susono, Japan

[73] Assignee: Toyota Jidosha Kabushiki Kaisha, Toyota, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/148,508

[22] Filed: Sep. 4, 1998

[30] Foreign Application Priority Data

Oct. 14, 1997 [JP] Japan ................................... 9-280684

[51] Int. Cl.$^7$ .............................. G01N 3/56; G01N 9/24; G01N 33/26; G01N 29/18
[52] U.S. Cl. ............................ 73/53.05; 73/10; 73/32 A; 73/54.41; 73/61.49
[58] Field of Search .............................. 73/53.05, 54.41, 73/61.49, 32 A, 10

[56] References Cited

U.S. PATENT DOCUMENTS

| | | | |
|---|---|---|---|
| 3,859,846 | 1/1975 | Asadia et al. | 73/53.05 |
| 4,320,659 | 3/1982 | Lynnworth et al. | 73/54.41 |
| 4,565,088 | 1/1986 | Crambes | 73/61.49 |
| 4,779,452 | 10/1988 | Cohen-Tenoudji et al. | 73/54.41 |
| 4,827,746 | 5/1989 | Kawaguchi | 73/32 A |
| 5,060,507 | 10/1991 | Urmson et al. | 73/597 |
| 5,255,564 | 10/1993 | Glad et al. | 73/597 |
| 5,271,267 | 12/1993 | Baumoel | 73/54.41 |
| 5,739,432 | 4/1998 | Sinha | 73/61.49 |
| 5,886,262 | 3/1999 | Sinha | 73/579 |
| 5,907,278 | 5/1999 | Park et al. | 73/53.05 |
| 5,987,972 | 11/1999 | Hirota et al. | 73/61.49 |

FOREIGN PATENT DOCUMENTS 7-225228  8/1995  Japan.

OTHER PUBLICATIONS

Susumu Sakagami, et al., Proceeding of the Scientific Meeting, No. 952, pp. 199 to 202, "Fuel Property Detection Using Fuel Density", May 1995 (with partial English translation).

*Primary Examiner*—Hezron Williams
*Assistant Examiner*—Chad Soliz
*Attorney, Agent, or Firm*—Oblon, Spivak, McClelland, Maier & Neustadt, P.C.

[57] ABSTRACT

The present invention relates to a sensor for detecting the degree of deterioration of oil, and more particularly, provides an oil deterioration sensor which can detect the deterioration of oil and/or the liquid surface of oil by utilizing the fact that the sound velocity of ultrasonic waves change according to the alkalinity of the oil, the oil deterioration sensor for determining deterioration characteristics of oil by utilizing ultrasonic waves, which is characterized in that a deterioration sensor reflecting surface for reflecting ultrasonic waves transmitted from an ultrasonic wave transmitting portion is placed in oil so as to detect deterioration of the oil, and characterized by comprising: an oil deterioration detecting portion for evaluating a transmission velocity of an ultrasonic wave in the oil by receiving ultrasonic waves from the aforesaid deterioration sensor reflecting surface and for evaluating a degree of deterioration of oil from said transmission velocity of the oil.

8 Claims, 7 Drawing Sheets

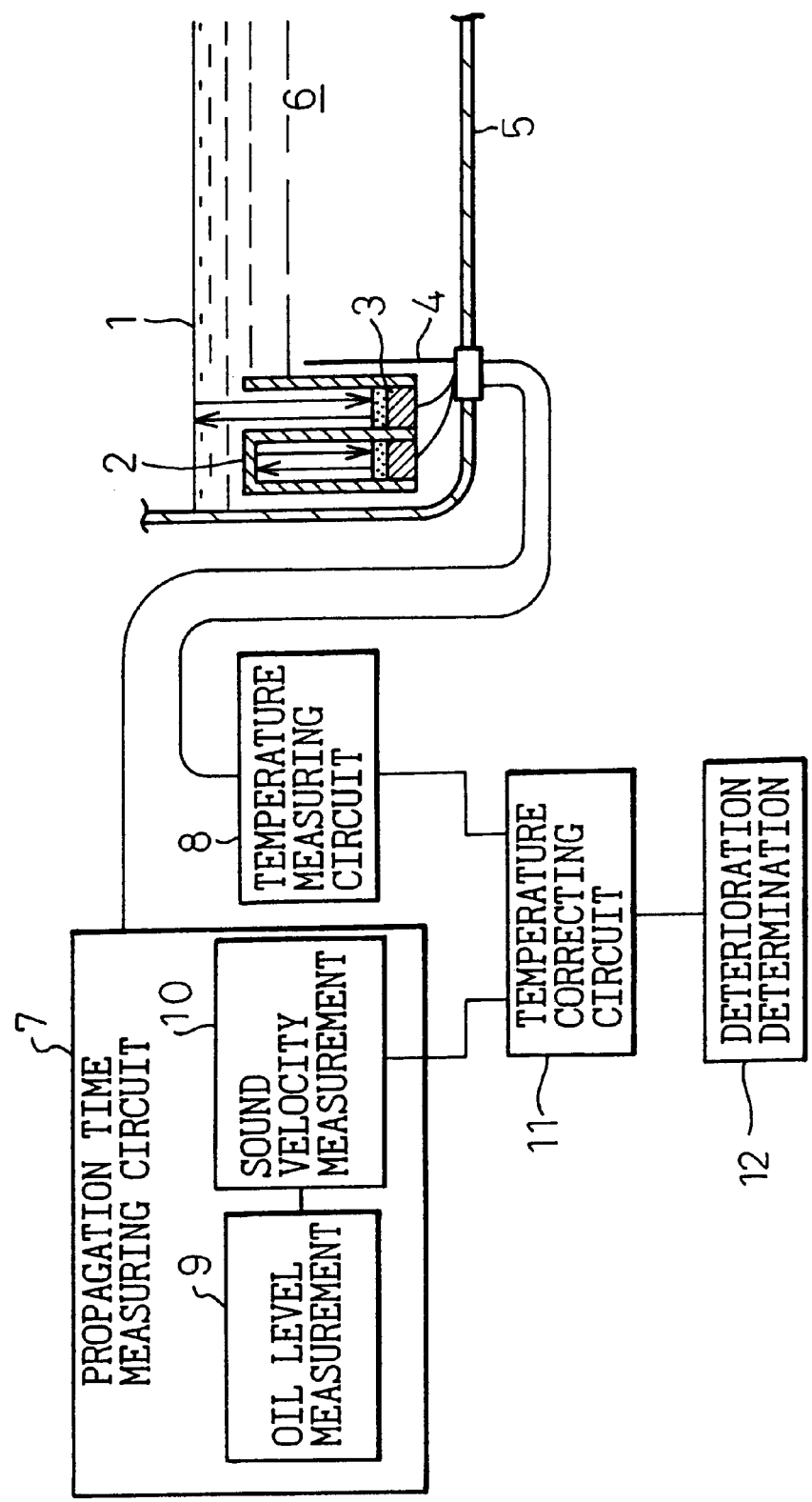

OIL DETERIORATION SENSOR

BACKGROUND OF THE INVENTION

1. Field of the Invention

The present invention generally relates to a sensor for detecting the degree of deterioration of oil, and more particularly, to an oil deterioration sensor being capable of detecting deterioration of oil and/or an oil level by utilizing the fact that the sound velocity of an ultrasonic wave varies with the alkalinity of oil.

2. Description of the Prior Art

Lubrication functions of engine oil for automobiles deteriorate owing to the deterioration of the oil itself, to combustion products of a fuel, and to dust, moisture and abrasion powder contained in intake air. Therefore, oil itself requires oxidation stability, acid corrosion-resistance and the suppression of generation of water and bubbles. A base number (namely, a total base number) serving as an index concerning various additives, which indicates an oil characteristic, is also an index to total basic components or ingredients, which is represented by an amount of potassium hydroxide needed for the neutralization of basic components contained in the oil. This index is effective in evaluating or determining the degree of deterioration of oil.

It is known that, especially in the case of engine oil for automobiles, such a base number controls the acid neutralization, which is employed as an engine-oil characteristic, and the oil deterioration characteristics, such as cleanliness, of engine oil. Hitherto, regarding the measurement of the density of gasoline for automobiles, for example, the Japanese Unexamined Patent Publication (Kokai) No. 7-225228 has disclosed the techniques of measuring a delay time to the transmission of an ultrasonic wave signal from an ultrasonic sensor, and then calculating the density of a fuel from this delay time and finally distinguishing the property thereof from this density.

However, the detection of the degree of deterioration of engine oil by the methods of measuring a delay speed of propagation of an ultrasonic wave has never been conducted. Even if it is intended to adopt such conventional methods, in the case that the deterioration of engine oil is detected from the strength of a reflected wave, the strength of the reflected wave is reduced when air bubbles are mixed in the oil. Thus, a detection error is caused. Consequently, it is substantially impossible to adopt the aforementioned conventional methods. Further, the temperature of the oil rises after an engine is started. Thus, the sound velocity of an ultrasonic wave changes. Consequently, in the case of the aforementioned techniques using ultrasonic waves, there is the necessity for using a high-precision thermometer that excels in response and resolution. Moreover, the equipment cost rises. Thus, there are such problems for the practical application of such conventional techniques. Therefore, the development of a sensor which utilizes ultrasonic waves as a relatively simple or convenient means for measuring the degree of deterioration of engine oil and has high responsibility and is advantageous in terms of the cost, has been desired.

SUMMARY OF THE INVENTION

An object of the present invention is to provide an oil deterioration sensor for determining the degree of deterioration of engine oil from the fact that the sound velocity changes according to the alkalinity of the oil, by utilizing ultrasonic waves in a sensor for determining the degree of deterioration of oil.

Further, another object of the present invention is to provide an oil deterioration sensor which can achieve the measurement of the degree of deterioration of oil and/or the detection of the liquid surface of the oil according to ultrasonic waves transmitted from at least one transducer, by utilizing ultrasonic waves, which is a relatively simple and convenient means for the measurement of the degree of deterioration of the oil and/or the detection of the liquid surface of the oil.

Furthermore, still an object of the present invention is to provide an oil deterioration sensor which can correct the sound velocity of the aforementioned ultrasonic wave through the utilization of a transducer, whose characteristics greatly change with temperature, by utilizing a method of enhancing the precision in measuring the sound velocity which is significantly affected by temperature.

The gist of the present invention is summarized as follows:

(1) An oil deterioration sensor for determining deterioration characteristics of oil by utilizing ultrasonic waves, characterized in that the transmission velocity of ultrasonic waves in oil is measured by transmitting and receiving ultrasonic waves in the oil, and that a degree of deterioration of the oil is detected from said transmission velocity of ultrasonic waves.

(2) An oil deterioration sensor which can distinguish deterioration characteristics or a liquid surface of oil by utilizing ultrasonic waves, characterized in that a deterioration sensor reflecting surface for reflecting ultrasonic waves transmitted from an ultrasonic wave transmitting portion is placed in the oil so as to detect deterioration of the oil, and comprising: an oil deterioration detecting portion for detecting a transmission velocity of an ultrasonic wave in the oil by receiving ultrasonic waves from said deterioration sensor reflecting surface and for detecting a degree of deterioration of oil from said transmission velocity of the oil; and an oil level detecting portion for transmitting ultrasonic waves from said ultrasonic wave transmitting portion to a liquid surface of the oil and for detecting a height of said liquid surface by receiving ultrasonic waves from said liquid surface.

(3) The oil deterioration sensor according to item (1) or (2), wherein a piezoelectric-crystal element, whose temperature characteristics abruptly change at a predetermined temperature, is used in the transducer.

(4) The oil deterioration sensor according to item (1) or (2), wherein said sensor is used for determining the kind of oil from the transmission velocity of the ultrasonic wave.

(5) The oil deterioration sensor according to item (2), wherein the ultrasonic waves are transmitted and received independently in the oil deterioration sensor reflecting surface and the liquid surface of oil.

(6) The oil deterioration sensor according to item (2), wherein the ultrasonic reflecting wave from the deterioration sensor reflecting surface is received by a transducer at the transmitting side, and the ultrasonic reflecting wave from the liquid surface of oil is received by a receiving-only transducer.

(7) The oil deterioration sensor according to item 2, wherein the reflecting ultrasonic waves from the deterioration sensor reflecting surface and the liquid surface of oil/are received by one transducer.

BRIEF DESCRIPTION OF THE DRAWINGS

FIG. 1 a diagram for showing an outline of a sensor and an apparatus of Example 1 according to the present invention.

FIG. 2(a) is a diagram showing a deterioration sensor; and FIG. 2(b) is a diagram showing an oil level sensor.

FIG. 4(a) is a diagram showing a deterioration sensor of Example 2; FIG. 4(b) is a diagram showing ultrasonic waves received from an oil level sensor of Example 2; and FIG. 4(c) is a diagram showing a deterioration sensor and an oil level sensor of Example 3;

FIG. 5(a) is a diagram showing an outline of one transducer; FIG. 5(b) is a diagram showing an outline of a transducer adapted to transmit ultrasonic waves upwardly and downwardly; and FIG. 5(c) is a diagram showing an outline of a sensor in the case that the strength of ultrasonic waves reflected from the liquid surface of oil is increased.

FIG. 6(a) is a diagram showing an outline of the apparatus; and FIG. 6(b) is a diagram showing ultrasonic waves transmitted and received by a transducer thereof.

FIG. 7(a) is a diagram showing the relationship between the sound velocity thereof and temperature.

FIG. 8(a) is a diagram showing a change in temperature of the oil; FIG. 8(b) is a diagram showing the temperature characteristics of a piezoelectric-crystal element; and FIG. 8(c) s a diagram showing the resistance characteristics of a thermistor.

FIG. 9(a) is a diagram showing an outline of an apparatus thereof; and FIG. 9(b) is a diagram showing the relationship between the value of the sound velocity in oil and the oil type.

DESCRIPTION OF THE PREFERRED EMBODIMENT

In the case of the first and second oil deterioration sensors of the present invention, the sound velocity of ultrasonic waves changes according to the alkalinity of oil, which reflects the deterioration of the oil. Thus, the deterioration of the oil can be detected by measuring this sound velocity. Further, both of the oil deterioration and the oil level can be simultaneously detected or determined by receiving ultrasonic waves reflected from the oil surface. Moreover, the sound velocity of ultrasonic waves varies with temperature and thus should be measured at a predetermined temperature. However, the need for a thermometer is eliminated by employing the constitution of the third oil deterioration sensor of the present invention.

Figure 7A:
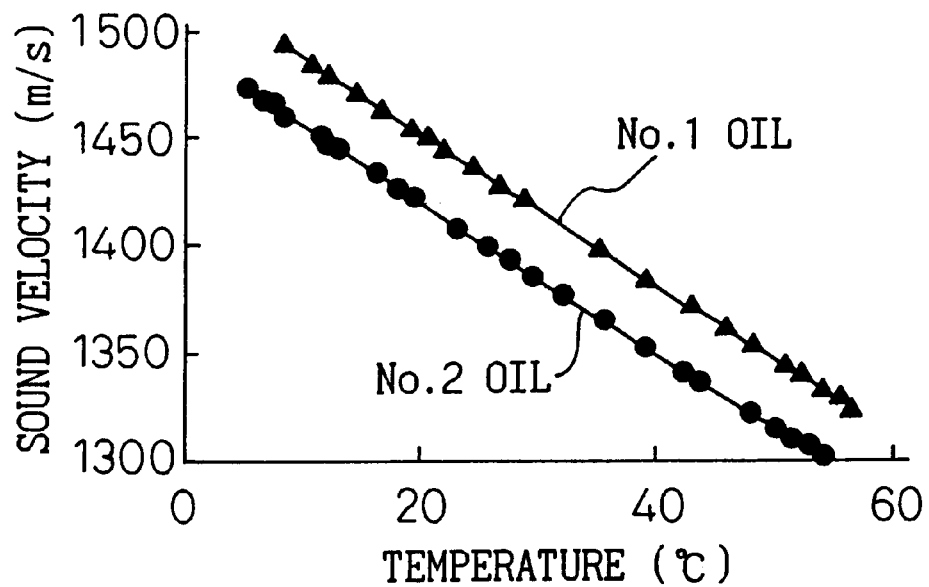
FIGS. 7(a) and (b) show sound-velocity propagation characteristic of ultrasonic waves in oil according to the present invention.
Figure 7B:
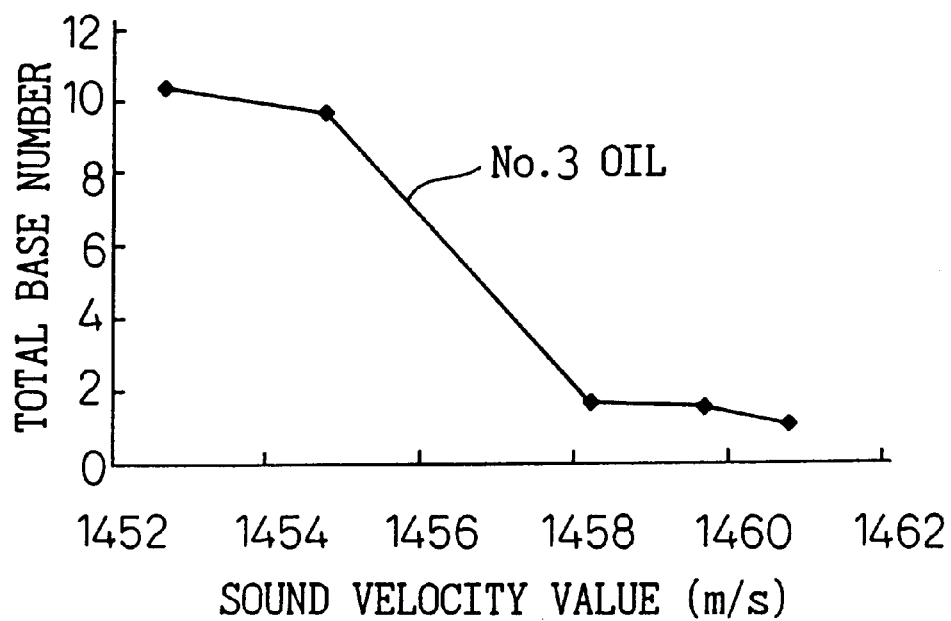
FIG. 7(b) is a diagram showing the relationship between the total base number and the sound velocity.

The inventors of the present invention have accomplished the present invention by acquiring the following knowledge by an experiment. Engine oil exhibits the propagation characteristics of ultrasonic waves therein as illustrated in FIGS. 7(a) and 7(b). Namely, as shown in FIG. 7(a), the sound velocity linearly decreases with the rise in temperature. This figure shows changes in the sound velocity, which respectively correspond to two different kinds of oil, No. 1 and No. 2.

On the other hand, according to the relationship between the total base number and the sound velocity in No. 3 oil as illustrated in FIG. 7(b), the sound velocity rises with the decrease in the total base number. In a range where the total base number is nearly 2 or less, this relationship tends to become more pronounced. However, this relationship can be represented by a nearly fixed or constant relation, on the average. The relations illustrated in these figures enable the sensor to detect and judge the degree of deterioration of oil by first correcting an actual measured value of the sound velocity to a value of the sound velocity at a certain temperature and by then finding a total base number corresponding to the sound velocity at the standard temperature at that time.

After the correction at that time, the sound velocity rises with the progress of deterioration of the oil. This is because, as is understood from the following expression; $C=(K/\rho)$ where C denotes the sound velocity; K a volume elasticity; and $\rho$ a density, the viscosity of the oil changes owing to the ablation of an oil additive and to the degradation of base oil. As a result, the volume elasticity rises. In other words, the sound velocity rises with reduction in the total base number which is an index of oil deterioration.

Next, a method of measuring temperature by using a piezoelectric element, whose temperature characteristics drastically change in a specific temperature region, according to the present invention will be described hereinbelow with reference to FIGS. 8(a), 8(b) and 8(c).

Figure 8A:
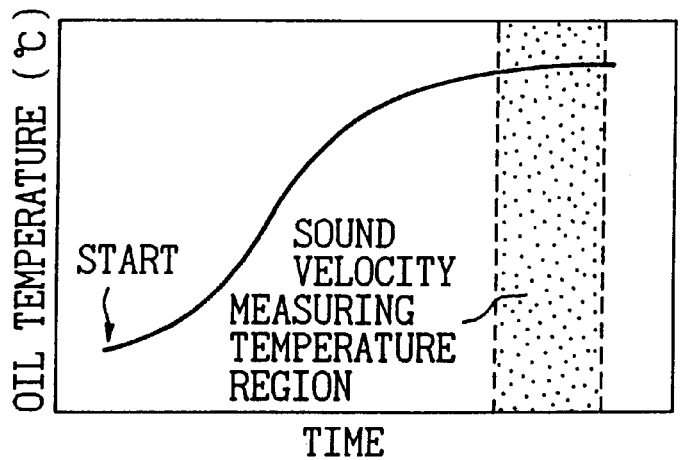
FIGS. 8(a)–8(c) show the temperature characteristics of oil according to the present invention.

As shown in FIG. 8(a), the temperature of the oil rises with time after an engine is started. Hitherto, a high-precision thermometer that excels in responsiveness and resolution has been needed for measuring temperature in a region where a change in temperature is large. However, if the sound velocity can be measured in a stable temperature range where this change in temperature is small, for instance, in the vicinity of 80° C. in the case of a normal operation mode, the influence of the change in temperature can be disregarded. Further, the sound velocity can be measured with good precision.

Figure 8B:
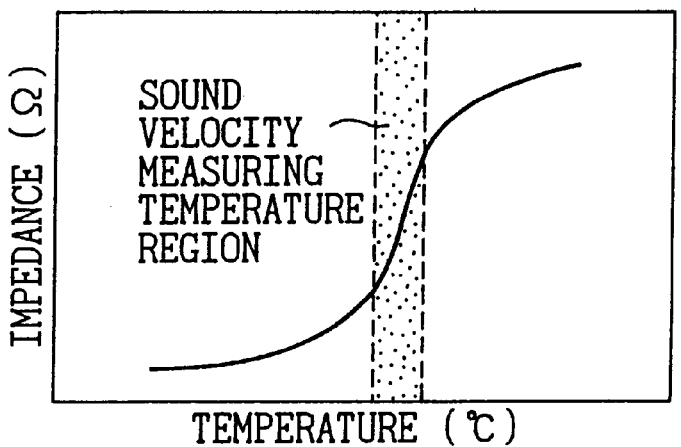
Figure 8C:
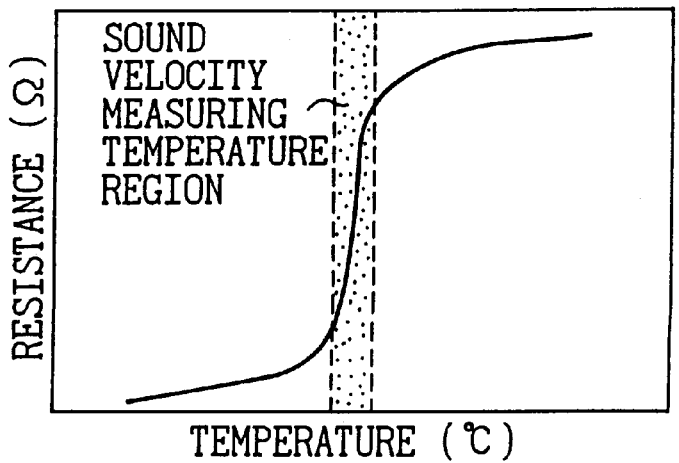

The high-accuracy measurement of temperature in a region, in which a change in temperature is small, can be achieved without providing a thermometer in the apparatus, by using a material whose impedance (or resonance frequency) largely changes with temperature in the aforementioned sound-velocity measuring temperature range as illustrated in FIG. 8(b).

Furthermore, the high-accuracy measurement of temperature can be attained by using a thermistor, whose resistance characteristics rapidly change in the proximity of a sound-velocity measuring temperature, to be employed as a semiconductor whose resistance largely changes according to temperature, for example, a PCT (polychlorinated terphenyl) thermistor which is usually employed in a temperature switch. In this case, simultaneously, the cost is considerably reduced. Additionally, the sensor of the present invention can be also used as a gasoline characteristic sensor and a gasoline level sensor, by inserting it into a gasoline tank.

Hereinafter, the present invention will be further described, in detail, with reference to the examples.

EXAMPLES

Example 1

This example of the present invention relates to an engine oil level/oil deterioration sensor and is adapted to transmit ultrasonic waves into oil and to receive ultrasonic waves reflected from a deterioration sensor reflecting surface and an oil surface.

FIG. 1 shows an outline of a device of this embodiment. An ultrasonic wave transmitting/receiving portion 3 of a transducer is provided in oil contained in an oil pan 5. As viewed in this figure, the ultrasonic wave transmitting/receiving portion transmits ultrasonic waves perpendicularly to the deterioration sensor reflecting surface 2 and the oil surface 1, respectively, independent of each other. Then, the ultrasonic wave transmitting/receiving portion receives ultrasonic waves reflected therefrom. Further, data representing a measured propagation time is inputted to a propagation time measuring circuit 7. Thereafter, data is outputted therefrom as data representing the results of measurements respectively performed by an oil level measurement portion 9 and a sound velocity measurement portion 10. Subsequently, oil temperature information is inputted by a temperature sensor 4 to a temperature measuring circuit 8. Then, the oil level and the sound velocity value are corrected according to the temperature indicated by the oil temperature information.

Figure 2A:
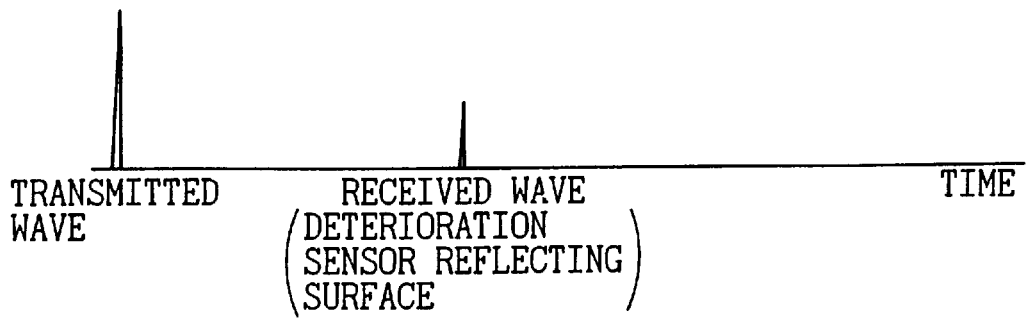
FIGS. 2(a) and 2(b) show ultrasonic waves transmitted and received by the sensor according to Example 1.
Figure 2B:
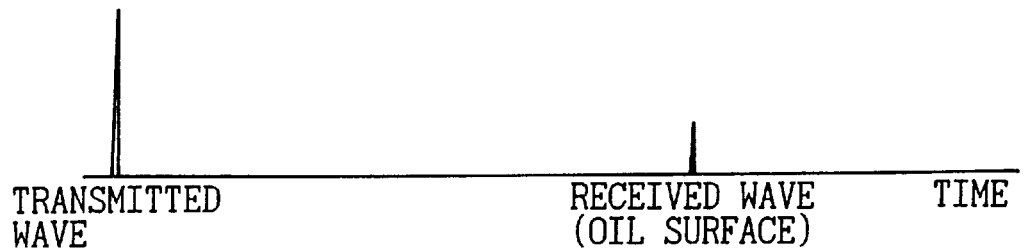

FIG. 2(a) shows ultrasonic waves reflected in a typical deterioration sensor side transducer. FIG. 2(b) shows ultrasonic waves reflected at a typical oil surface side transducer. Namely, in the case of this embodiment, a result of the detection or determination of oil deterioration is obtained by measuring the sound velocity of ultrasonic waves, which are reflected on the reflecting surface of the deterioration sensor and return to the ultrasonic wave transmitting/receiving portion in oil. Further, a result of the determination of the oil level is obtained by finding the values of the sound velocity and the propagation time from ultrasonic waves, which are reflected on the oil surface and return to the ultrasonic wave transmitting/receiving portion, in oil and by determining or measuring the distance between this portion and the oil surface from such values of the sound velocity and the propagation time.

Example 2

This example is a sensor obtained as a modification of Example 1 by employing a single transducer instead of two ultrasonic wave transmitting transducers in Example 1. In the case of Example 2, some of the ultrasonic waves transmitted from the transducer, which are reflected by the reflecting surface of the deterioration sensor, are received by the transmitting transducer, while the other part of the ultrasonic waves transmitted from the transducer, which are reflected by the boundary surface (namely, the liquid surface) between the oil and air, are received by a receive-only transducer.

Figure 3:
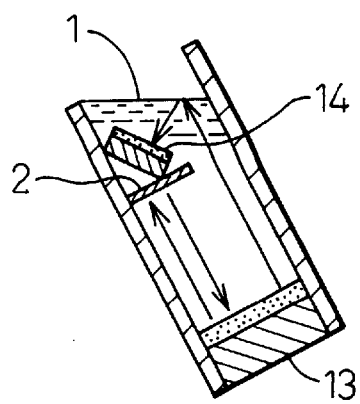
FIG. 3 is a diagram for showing an outline of a sensor and an apparatus according to Example 2 of the present invention.
Figure 4A:
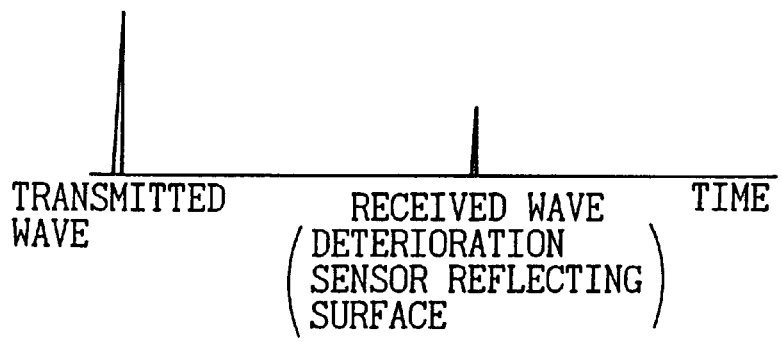
FIGS. 4(a)–4(c) show ultrasonic waves transmitted and received by the sensor according to Examples.
Figure 4B:
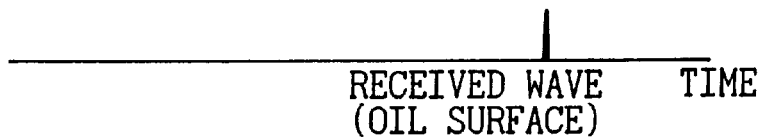

FIG. 3 shows an outline of the device according to this example. Ultrasonic wave transmitting/receiving portions of the transducers 13 and 14 are obliquely provided in the oil. As shown in this figure, ultrasonic waves are simultaneously transmitted to the deterioration sensor reflecting surface 2 and the oil surface 1 from a direction inclined to a vertical direction. Further, ultrasonic waves reflected from the reflecting surface 2 and the oil surface 1 are respectively received by transducers 13 and 14, independent of each other. Thus, the transducer 14 is a receive-only transducer. FIG. 4(a) shows ultrasonic waves reflected at a typical deterioration sensor transducer. FIG. 4(b) shows ultrasonic waves reflected at a typical oil surface transducer. Namely, in the case of this embodiment, a result of the detection of oil deterioration is obtained by measuring the sound velocity of ultrasonic waves, which are reflected on the reflecting surface of the deterioration sensor and return to the ultrasonic wave transmitting/receiving portion, in the oil. Further, a result of the determination of the oil level is obtained by finding the values of the sound velocity and the propagation time from ultrasonic waves, which are reflected on the oil surface and return to the ultrasonic wave receiving transducer 14 in the oil, and by measuring the distance between this portion and the oil surface from such values of the sound velocity and the propagation time.

Example 3

In the case of a sensor of this example, a single transducer serves both as the deterioration sensor transducer and the oil surface transducer.

Figures 5A, 5B, 5C:
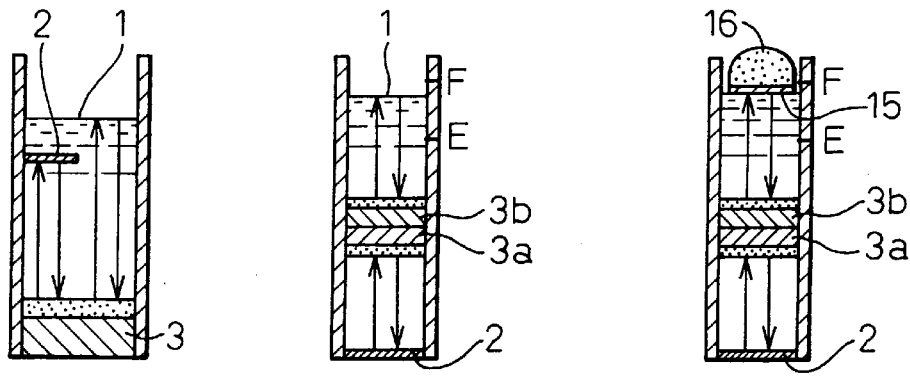
FIGS. 5(a)–5(c) show a sensor and an apparatus according to example of the present invention.

FIGS. 5(a), 5(b) and 5(c) show an outline of a device or sensor of this example. In the case of the device of FIG. 5(a), a transducer 3 is provided with a deterioration sensor reflecting plate 2 whose diameter is almost ½ of that of a transducer 3 or less. Further, in the case of the device of FIG. 5(b), each of transducers 3a and 3b may be of the two-piece type or may be a single transducer of the type that can radiate ultrasonic waves from both sides thereof. Moreover, each of the transducers 3a and 3b can transmit ultrasonic waves from both sides thereof. Furthermore, the sensor is provided with a deterioration sensor reflecting plate 2 on the bottom surface side. In this case, the outside diameter of the sensor can be decreased. In the case of the device of FIG. 5(c), each of transducers 3a and 3b can transmit ultrasonic waves from both sides thereof, similarly as in the case of the device of FIG. 5(b). Further, the sensor is provided with a deterioration sensor reflecting plate 2. Furthermore, a float 16 is provided at the liquid surface side of the sensor. Additionally, a reflecting plate 15 is provided on the bottom surface of the float 16. In this case, the strength of ultrasonic waves reflected from the liquid surface can be enhanced by immersing the reflecting surface mounted on the float in the oil.

Figure 4C:
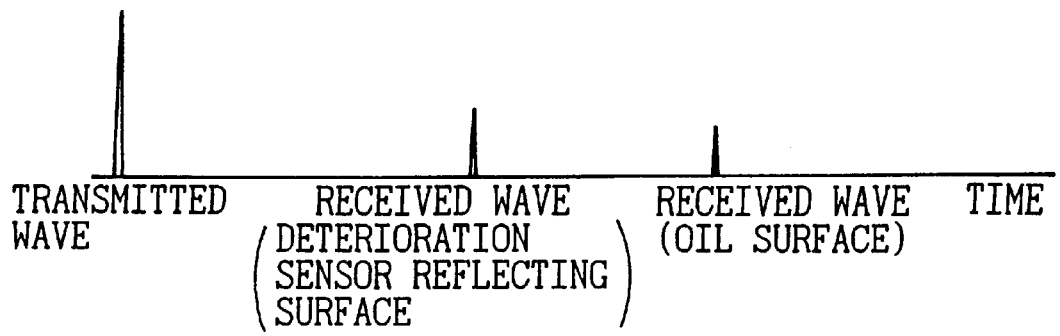

In all cases, ultrasonic waves respectively transmitted perpendicularly from a transducer are reflected by the deterioration sensor reflecting plate and the liquid surface independently of each other and are received by a same transducer. FIG. 4(c) shows ultrasonic waves reflected at a typical deterioration sensor side transducer and at a typical oil level sensor side transducer. Namely, in the case of this example, a result of the detection or determination of oil deterioration is obtained by measuring the sound velocity of ultrasonic waves, which are reflected on the reflecting surface of the deterioration sensor and return to the ultrasonic wave transmitting/receiving portion, in the oil. Further, a result of the determination of the oil level is obtained by finding the values of the sound velocity and the propagation time from ultrasonic waves which are reflected on the oil surface and return to the ultrasonic wave transmitting/receiving portion in the oil and by determining the distance between this portion and the oil surface from the values of the sound velocity and the propagation time.

Example 4

This example of the present invention relates to an engine oil deterioration sensor and is adapted to transmit ultrasonic waves into oil and to receive ultrasonic waves reflected from a deterioration sensor reflecting surface.

Figure 6A:
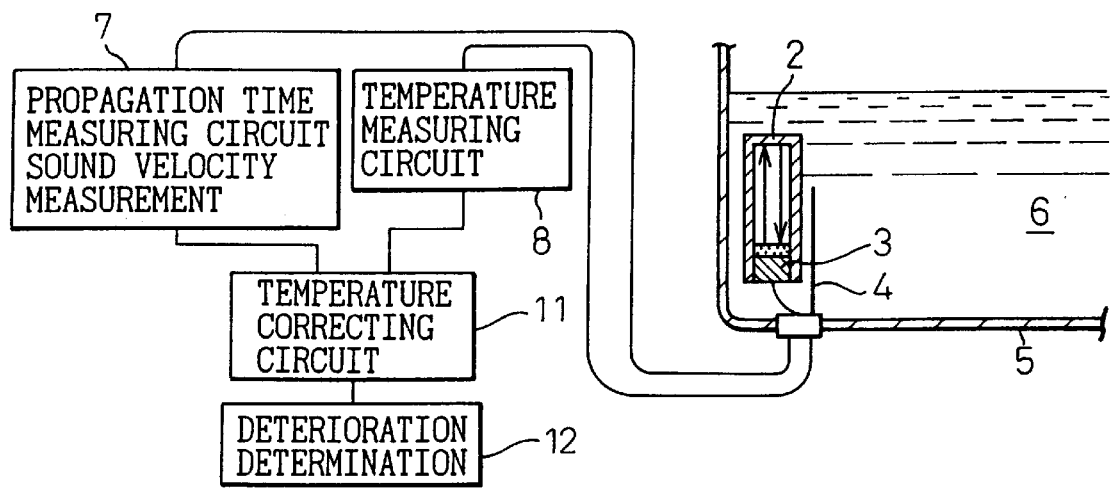
FIGS. 6(a) and 6(b) show a sensor, an apparatus and ultrasonic waves transmitted and received in Example 4 according to the present invention.

FIG. 6(a) shows an outline of a device of this example. This device has a constitution consisting of a transducer for transmitting and receiving ultrasonic waves, a temperature sensor for measuring the temperature of oil at the time of sensing, a reflecting surface for maintaining the propagation distance of ultrasonic waves at a constant value, and an electronic circuit portion for measuring a propagation time.

Practically, the ultrasonic wave transmitting/receiving portion of the transducer 3 is provided in an oil 6 that is contained in an oil pan 5. As viewed in this figure, the ultrasonic wave transmitting/receiving portion transmits ultrasonic waves perpendicularly to the deterioration sensor reflecting surface 2. Then, the ultrasonic wave transmitting/receiving portion receives ultrasonic waves reflected therefrom. Further, data representing a measured propagation time is inputted to a propagation time measuring circuit 7. Thereafter, data is outputted therefrom as data representing results of measurements performed by a sound velocity measurement portion. Subsequently, oil temperature information is inputted by a temperature sensor 4 to a temperature measuring circuit 8 and a temperature correcting circuit 11. Then, the sound velocity value is corrected according to the temperature indicated by the oil temperature information. Further, the degree of deterioration of the oil is determined or judged.

Figure 6B:
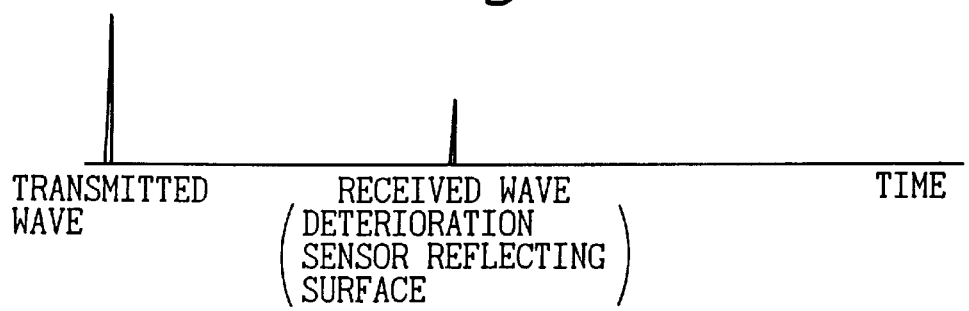

FIG. 6(b) shows ultrasonic waves reflected at a typical deterioration sensor side transducer. Namely, in the case of this embodiment, the result of the detection or determination of oil deterioration is obtained by measuring the sound velocity of ultrasonic waves, which are reflected on the reflecting surface of the deterioration sensor and return to the ultrasonic wave transmitting/receiving portion, in the oil. Then, the temperature correction is performed on the sound velocity so that the sound velocity is changed into the value of the sound velocity at a reference temperature. After the correction, the sound velocity rises with the progress of deterioration of the oil. Thus, a judgement on the deterioration of the oil can be made.

According to the relationship between the total base number and the sound velocity in the oil as illustrated in FIG. 7(b), the sound velocity rises with a decrease in the total base number. In a range where the total base number is nearly 2 or less, this relationship tends to become more pronounced. However, this relationship can be represented by a nearly constant relation, on the average. The relations illustrated in these figures enable the sensor to detect and judge the degree of deterioration of oil by first correcting an actual measured value of the sound velocity into the value of the sound velocity at a certain temperature and by then finding a total base number corresponding to the sound velocity at the standard temperature at that time.

After the correction at that time, the sound velocity rises with the progress of deterioration of the oil. This is because the viscosity of the oil changes owing to the ablation of an oil additive and to the degradation of the base oil, as is understood from the aforementioned expression representing the sound velocity, and consequently, the volume elatisticity rises. In other words, the sound velocity rises with reduction in the total base number which is an index of oil deterioration. Thus, no sound-velocity change is caused due to bubbles contained in the oil. Consequently, the measurement of the sound velocity can be achieved with good precision.

Example 5

Figure 9A:
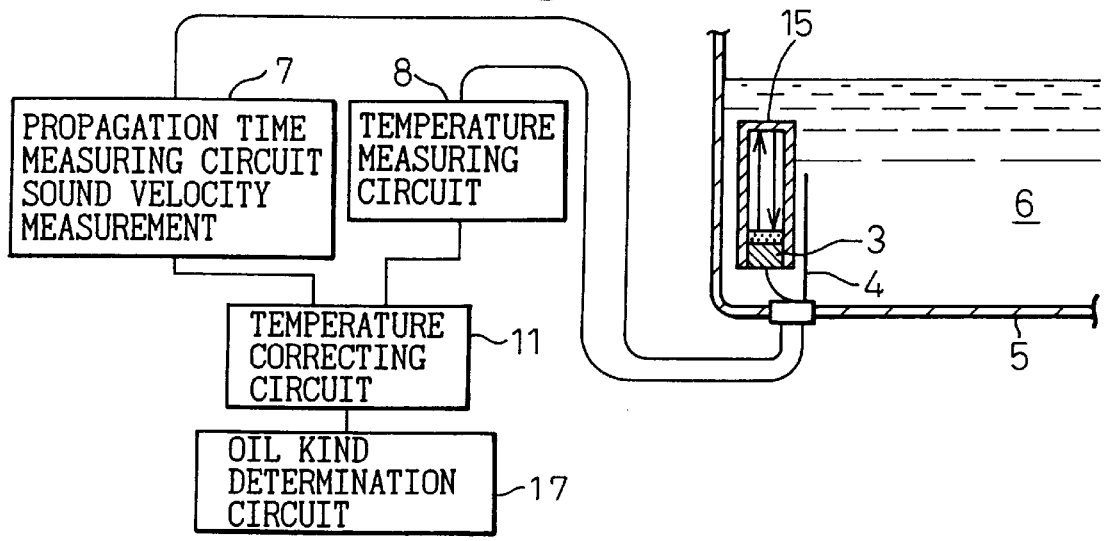
FIGS. 9(a) and 9(b) illustrate Example 5 of the present invention.

This example is a sensor for determining whether an oil is synthetic oil or mineral oil, by measuring the sound velocity of ultrasonic waves in the oil. FIG. 9(a) shows an outline of a device of this example. This device has a constitution consisting of a transducer for transmitting and receiving ultrasonic waves, a temperature sensor for measuring the temperature of oil at the time of sensing, a reflecting surface for maintaining the propagation distance of ultrasonic waves at a constant value, and an electronic circuit portion for measuring a propagation time.

Practically, the ultrasonic wave transmitting/receiving portion of the transducer 3 is provided in an oil 6 that is contained in an oil pan 5. As viewed in this figure, the ultrasonic wave transmitting/receiving portion transmits ultrasonic waves perpendicularly to a reflecting surface 15, independent of each other. Then, the ultrasonic wave transmitting/receiving portion receives ultrasonic waves reflected therefrom. Further, data representing a measured propagation time is inputted to a propagation time measuring circuit 7. Thereafter, data is outputted therefrom as those representing results of measurements performed by a sound velocity measurement portion. Subsequently, oil temperature information is inputted by a temperature sensor 4 to a temperature measuring circuit 8 and a temperature correcting circuit 11. Then, the sound velocity value is corrected according to the temperature represented by the oil temperature information. Further, the kind of the oil is determined or judged by an oil type judgement circuit 17.

Figure 9B:
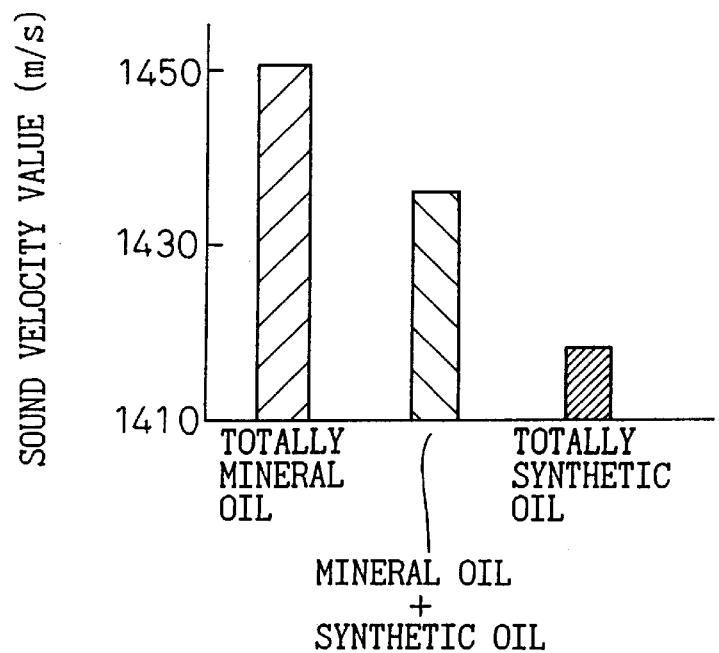

This determining method is based on the fact that the values of the sound velocity, which respectively correspond to the cases that the oil is totally synthetic oil, that the oil is totally mineral oil and that the oil is a mixture of synthetic oil and mineral oil, are different from one another, as shown in FIG. 9(b). It is evident from this data that the kind of oil can be determined by measuring the sound velocity value. Generally, the volume elasticity and the density of oil varies with the type of oil. Thus, a difference in the kind of oil results in a difference in the measured value of the sound velocity of ultrasonic waves propagating therethrough.

The synthetic oil and the mineral oil are different from each other in characteristics such as a viscosity index, low-temperature performance, and heat stability. Thus, these kinds of oil are different in service-life warranty period from each other. It is, however, difficult to predict the useful service-life warranty period of the mixture of these kinds of oil. As a result of application of this example, this service-life warranty period can be changed according to the kind of oil. Namely, in accordance with a method of the present invention, the deterioration characteristics and the useful service-life warranty period of the oil can be more easily and simply changed with good accuracy by measuring the sound velocity of ultrasonic waves in the oil.

In accordance with the sensor of the present invention, the alkalinity corresponding to the degree of deterioration of oil can be simply and easily detected by measuring the sound velocity of ultrasonic waves. Moreover, simultaneously, the oil level can be detected by altering the arrangement and combination of transducers. Furthermore, the characteristics and the liquid surface level of gasoline can be detected or determined by dipping the sensor of the present invention into a gasoline tank.

We claim:

1. An oil deterioration sensor which can distinguish deterioration characteristics or a liquid surface of oil by utilizing ultrasonic waves, characterized in that a deterioration sensor reflecting surface for reflecting ultrasonic waves transmitted from an ultrasonic wave transmitting portion is placed in oil so as to detect deterioration of the oil, and comprising: an oil deterioration detecting portion for detecting a transmission velocity of an ultrasonic wave in the oil by receiving ultrasonic waves from said deterioration sensor reflecting surface and for determining a base number of the oil as a measure of a degree of deterioration of oil from said transmission velocity of the oil; and an oil level detecting portion for transmitting ultrasonic waves from said ultrasonic wave transmitting portion to an air-liquid liquid surface of the oil and for detecting a height of said liquid surface by receiving ultrasonic waves from said liquid surface.

2. The oil deterioration sensor according to claim 1, wherein a piezoelectric-crystal element, whose temperature characteristics abruptly change at a predetermined temperature, is used in the sensor element.

3. The oil deterioration sensor according to claim 1 or 2, wherein said sensor is used for determining the kind of oil from the transmission velocity of the ultrasonic wave.

4. The oil deterioration sensor according to claim 1, wherein the ultrasonic waves are transmitted and received independently.

5. The oil deterioration sensor according to claim 1, wherein the ultrasonic reflecting wave from the deterioration sensor reflecting surface is received by a transducer at a transmitting side thereof, and the ultrasonic reflecting wave from the liquid surface of oil is received by a receiving-only transducer.

6. The oil deterioration sensor according to claim 1, wherein the reflecting ultrasonic waves from the deterioration sensor reflecting surface and the liquid surface of oil are received by only one transducer.

7. An oil deterioration sensor for determining deterioration characteristics of oil by utilizing ultrasonic waves, comprising a sensor element positioned to measure the transmission velocity of ultrasonic waves in oil by transmitting and receiving ultrasonic waves in the oil, and means for determining a base number of the oil as a measure of a degree of deterioration of the oil from the measured transmission velocity of ultrasonic waves.

8. The oil deterioration sensor of claim 7, wherein the sensor element comprises a piezoelectric-crystal element having output characteristics which abruptly change at a predetermined temperature.

* * * * *